United States Patent
Ghosh et al.

(10) Patent No.: US 7,662,737 B2
(45) Date of Patent: Feb. 16, 2010

(54) BOUND PHOSPHORUS-MODIFIED ZEOLITE CATALYST, METHOD OF PREPARING AND METHOD OF USING THEREOF

(75) Inventors: Ashim Kumar Ghosh, Houston, TX (US); Pamela Harvey, Missouri, TX (US); Neeta Kulkarni, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 418 days.

(21) Appl. No.: 11/316,334

(22) Filed: Dec. 22, 2005

(65) Prior Publication Data

US 2007/0149384 A1 Jun. 28, 2007

(51) Int. Cl.
*B01J 29/06* (2006.01)
*C07C 2/66* (2006.01)

(52) U.S. Cl. .............. 502/63; 502/64; 502/71; 502/77; 585/446; 585/466; 585/467

(58) Field of Classification Search .......... 502/63, 502/64, 71, 77; 585/446, 466, 467
See application file for complete search history.

(56) References Cited

U.S. PATENT DOCUMENTS

| | | | |
|---|---|---|---|
| 5,380,690 A | 1/1995 | Zhicheng et al. | |
| 5,907,073 A | 5/1999 | Ghosh | |
| 6,047,544 A | 4/2000 | Yamamoto et al. | |
| 6,255,243 B1 * | 7/2001 | Drake et al. | 502/68 |
| 6,399,530 B1 | 6/2002 | Chen et al. | |
| 6,423,879 B1 * | 7/2002 | Brown et al. | 585/467 |
| 6,504,072 B1 | 1/2003 | Brown et al. | |
| 6,566,293 B1 | 5/2003 | Vogt et al. | |
| 6,943,131 B1 | 9/2005 | Ghosh et al. | |
| 7,084,318 B2 | 8/2006 | Ghosh et al. | |
| 7,279,608 B2 | 10/2007 | Ghosh et al. | |
| 7,304,194 B2 | 12/2007 | Ghosh et al. | |
| 2005/0070749 A1 * | 3/2005 | Ghosh et al. | 585/467 |
| 2005/0209492 A1 * | 9/2005 | Ghosh et al. | 585/467 |
| 2005/0239635 A1 | 10/2005 | Ghosh et al. | |
| 2005/0240070 A1 | 10/2005 | Ghosh et al. | |
| 2007/0032690 A1 | 2/2007 | Ghosh et al. | |

FOREIGN PATENT DOCUMENTS

WO 2005/033071 * 4/2005

* cited by examiner

*Primary Examiner*—Elizabeth D Wood
(74) *Attorney, Agent, or Firm*—Jim Wheelington

(57) ABSTRACT

Disclosed is a bound phosphorus-modified zeolite catalyst. Zeolite is treated with a phosphorus compound to form the phosphorus-treated zeolite. Binder material is treated with a mineral acid prior to being bound with the phosphorus-modified zeolite. The binder material includes inorganic oxide materials, such as alumina, clay, aluminum phosphate and silica-alumina, in particular, a binder of alumina or clay or their combinations. The mineral acid includes hydrochloric acid, nitric acid, phosphoric acid or sulfuric acid. The phosphorus-treated zeolite is combined with the acid-treated inorganic oxide binder material to form a zeolite-binder mixture. Water is added to form an extrudable paste which maybe shaped and is heated to a temperature of about 400° C. or higher to form a bound phosphorus-modified zeolite catalyst. For aromatic alkylation, the bound phosphorus-modified zeolite catalyst is contacted with an aromatic alkylation feed of an aromatic compound and an alkylating agent under reaction conditions suitable for aromatic alkylation.

62 Claims, 2 Drawing Sheets

BOUND PHOSPHORUS-MODIFIED ZEOLITE CATALYST, METHOD OF PREPARING AND METHOD OF USING THEREOF

BACKGROUND OF THE INVENTION

1. Field of the Invention

The invention relates generally to the alkylation of aromatic compounds and catalysts used for such reactions and their preparation.

2. Description of the Prior Art

Before 1940 virtually all of the aromatic solvents, including xylene, were produced from coal. Thereafter production of xylene from petroleum started. Most mixed xylene is currently produced by catalytic reforming of petroleum aromatic-rich streams from refineries. It is also obtained from pyrolysis gasoline as a by-product of olefin manufacture during the cracking of hydrocarbons, by-product of naphtha cracking. Xylene can also be obtained from toluene by disproportionation or alkylation. Toluene disproportionation (TDP) is a catalytic reaction of toluene to produce xylenes and benzene. Toluene methylation (TM) is a catalytic reaction of toluene with methanol to produce xylenes as shown below:

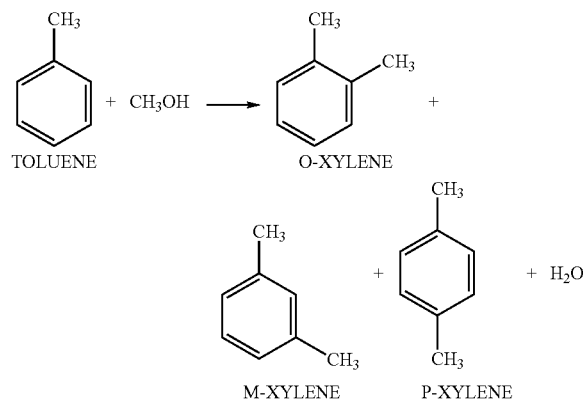

All of these processes generally produce a mixture of isomers. The xylene isomers, meta-xylene (m-xylene), ortho-xylene (o-xylene) and para-xylene (p-xylene), are important chemical intermediates. o-Xylene is oxidized to make phthalic anhydride which is used to make phthalate plasticizers among other things. m-Xylene is oxidized to make isophthalic acid, which is used in unsaturated polyester resins (UPR). However, p-xylene has by far the largest market of the three isomers. The largest use of p-xylene is in its oxidation to make terephthalic acid. Terephthalic acid is used in turn to make polymers such as polyethylene terephthalate (PET) and polybutylene terephthalate (PBT). PET is one of the largest volume polymers in the world. As such the demand for p-xylene is several times that for m- and o-xylene. In commercial manufacture p-xylene is purified from mixed xylenes by crystallization and adsorption processes.

Thermodynamic equilibrium compositions of o-, m-, and p-xylenes are approximately 25, 50 and 25%, respectively, at 500° C. The catalytic processes such as TDP and TM would give about 25% p-xylene (PX) in mixed-xylenes (MX). However, if a catalyst possesses shape selective properties it will give significantly greater than 25% PX. Typically, a shape selective catalyst would give >85% PX in MX.

Zeolites are crystalline solids made up of aluminum-substituted $SiO_4$ tetrahedral units joined together to form different ring and cage structures into a crystalline framework. The physical structure of zeolite is very porous with a large internal and external surface area. The substitution of aluminum generates a charge imbalance which must be countered by a supplementary counterion, such as a proton.

Zeolites can be shape-selective catalysts due to steric and electronic effects. Selective reactions can occur over zeolites as certain products, reactants or transition states are kept from forming within the pores either by transition state selectivity or because of size or shape of molecular diameter. By varying the preparation of zeolite catalysts, they can be modified to carry out very specific syntheses of desired products.

Modified zeolite catalysts are known for alkylation of aromatics, specifically methylation of toluene to xylenes, especially p-xylene

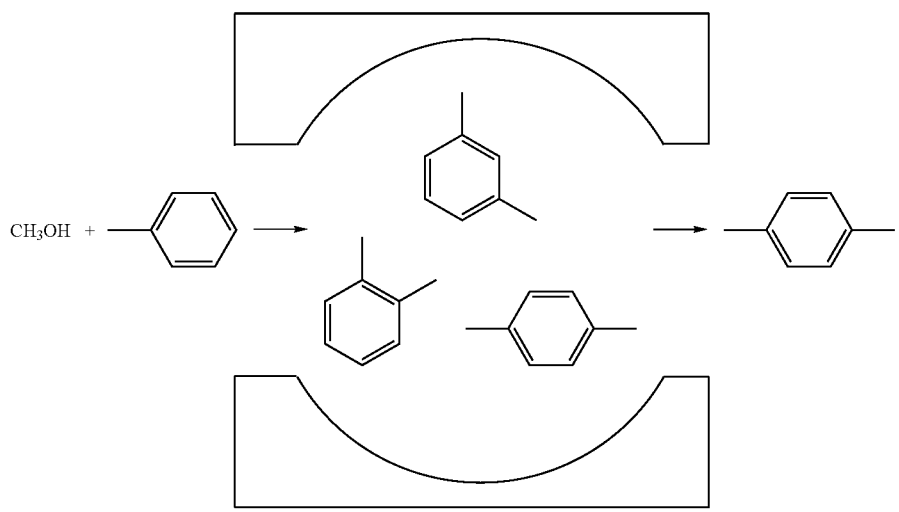

U.S. Pat. No. 6,504,072 discloses a phosphorus-modified zeolite used in the selective methylation of toluene to p-xylene. The P-modified zeolite catalyst may contain active and inactive materials such as clays, silica and/or metal oxides such as alumina as a binder. There is no disclosure of modification or treatment of the binder and no disclosure of the effect of modification or treatment of the binder on selectivity to para-xylene.

Other prior art discloses the modification or treatment of binder material for zeolite catalysts used in other processes.

U.S. Pat. No. 5,907,073 discloses a process for alkylation of an aromatic with a molecular sieve catalyst of a modified zeolite beta having an intergrowth of a ZSM-12 crystalline framework. During synthesis, $NH_4$-Beta and $LaNH_4$-Beta were mulled with nitric acid treated alumina, extruded and calcined which converted the $NH_4$-Beta and $LaNH_4$-Beta into H-Beta catalyst and LaH-Beta catalyst, respectively. The finished catalyst was used in ethylation of benzene to form ethylbenzene. There is no disclosure that modification or treatment of the binder had an effect on selectivity.

U.S. Pat. No. 5,380,690 discloses a catalyst for the production of light olefins which is a mixture of clay, inorganic oxides and zeolite prepared by mixing the precursor of the inorganic oxides such as aluminum sol, pseudo-bohemite, silica sol or its mixture, and silica-alumina sol or gel with clay, peptizing with de-cationized water to prepare a slurry, further mixing homogeneously, adjusting and maintaining the pH value of the slurry to 2-4 using inorganic acid such as hydrochloric acid, nitric acid, phosphoric acid, or sulfuric acid, after aging statically, adding into it a pre-calculated amount of zeolite, homogenizing, spray drying, washing-off isolated sodium ions, and drying. There is no disclosure that adjusting and maintaining the pH of the slurry containing the binder precursor had an effect on selectivity.

U.S. Pat. No. 6,047,544 discloses an engine exhaust gas purification catalyst of a layer of palladium, platinum or rhodium on a layer of a zeolite hydrocarbon adsorbent on a monolithic substrate. During synthesis, Pd-impregnated alumina powder, Pd-impregnated cerium oxide powder, nitric acid acidified alumina sol and water were introduced into a magnetic ball mill to crush the mixture so as to obtain a slurry. The nitric acid acidified alumina sol was obtained by adding 10 weight % nitric acid to 10 weight % bemite alumina. There is no disclosure that modification or treatment of the alumina had an effect on selectivity.

U.S. Pat. No. 6,399,530 discloses a hydrocracking catalyst having a binder of a small pore alumina which is peptized with nitric acid and has a specific surface area of 240-280 $m^2/g$ and a pore volume of 0.4-0.5 ml/g. There is no disclosure that modification or treatment of the alumina binder had an effect on selectivity.

U.S. Pat. No. 6,566,293 discloses an olefin-selective catalyst for production of light olefins which is a phosphorus-modified zeolite having a binder. The alumina binder is usually peptized before or during its combination with the other catalyst composition components. There is no disclosure that peptization of the alumina binder was with a mineral acid or that peptization of the alumina binder had an effect on selectivity.

SUMMARY OF THE INVENTION

A bound zeolite catalyst is a zeolite treated with a phosphorus compound to form a phosphorus-treated zeolite and an inorganic oxide binder material treated with a mineral acid. The catalyst can be made by combining a phosphorus-treated zeolite with an inorganic oxide binder material which has been treated with a mineral acid to form a zeolite-binder mixture and heating the zeolite-binder mixture at temperature of about 400° C. or higher to form a bound zeolite catalyst. The bound phosphorus-modified zeolite catalyst can be used in a process for alkylation of aromatics, such as methylation of toluene to xylenes, by contacting the bound zeolite catalyst with an aromatic compound and an alkylating agent under reaction conditions suitable for aromatic alkylation.

BRIEF DESCRIPTION OF THE DRAWINGS

A more complete appreciation of the invention and many of the associated and resultant advantages thereof will be readily understood by reference to the following detailed description when considered in connection with the accompanying drawings in which like numerals in different figures represent the same structures or elements wherein.

DETAILED DESCRIPTION OF THE INVENTION

Figure 1:
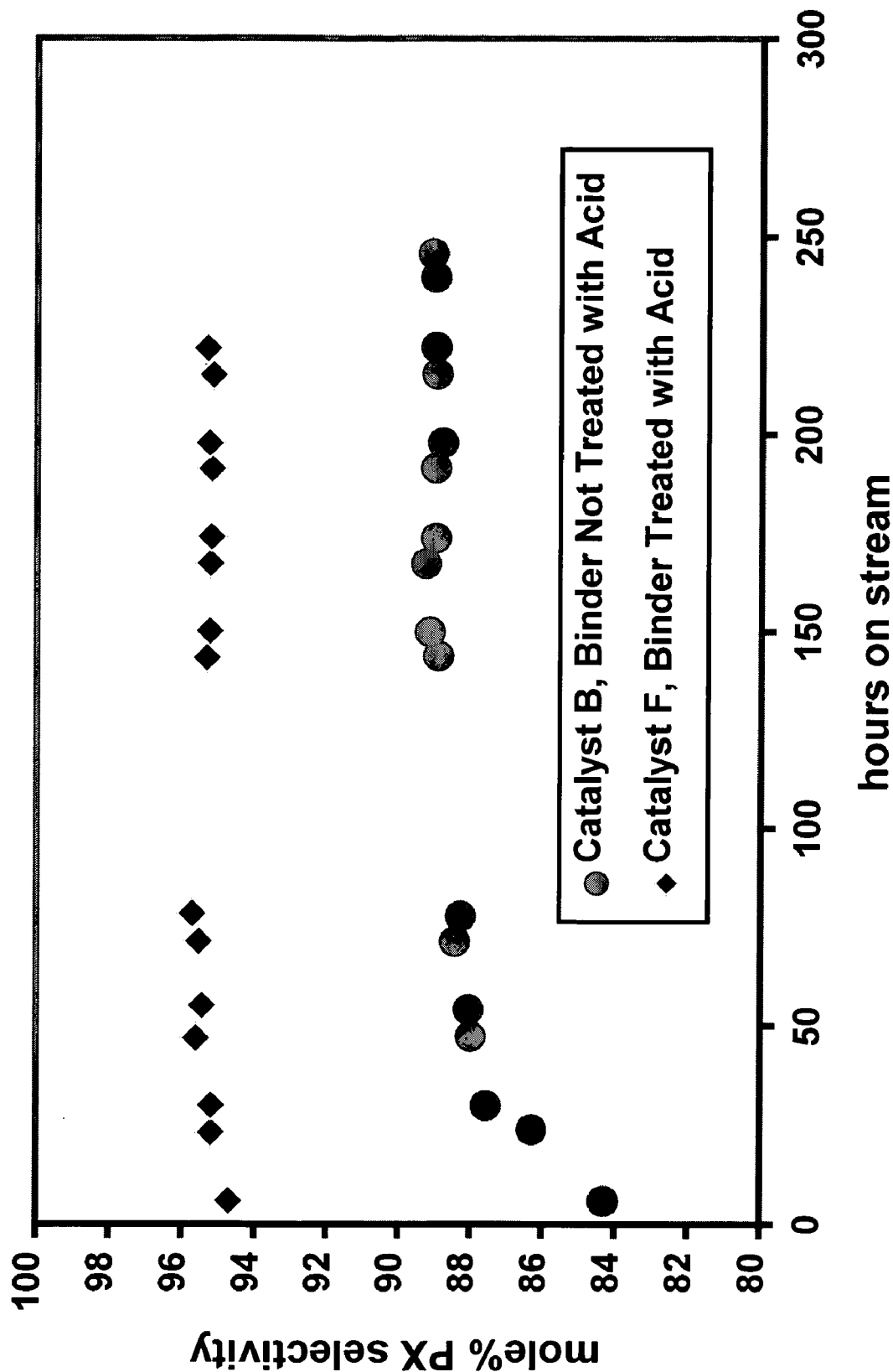
FIG. 1 is a plot of p-xylene selectivity as a function of time on stream for the toluene methylation reaction for catalysts B of Example 2 and catalyst F of Example 6.

Toluene methylation is known to occur over zeolite or zeolite-type catalysts, in particular, ZSM-5-type zeolite catalysts. Generally, a thermodynamic equilibrium mixture of ortho (o)-, meta (m)- and para (p)-xylenes is formed from the methylation of toluene. Thermodynamic equilibrium compositions of o-, m-, and p-xylenes may be around 25, 50 and 25 mole %, respectively, at a reaction temperature of about 500° C. Such toluene methylation may occur over at wide range of temperatures, however.

A high purity grade (99+%) p-xylene is desirable for its oxidation to terephthalic acid process. Thus, an increased concentration of p-xylene over equilibrium is desirable. However, production cost for such a concentration can be very high. p-Xylene can be separated from mixed xylenes by cycle of adsorption and isomerization which must be repeated many times because of its low isomeric concentration in the equilibrium mixture. If the concentration of p-xylene is higher than equilibrium, the high purity grade p-xylene can be more easily attained. An amount of p-xylene significantly higher than equilibrium can be obtained if the catalyst contains shape selective properties. Such shape selective properties can be incorporated in zeolite catalyst by modifying the zeolite.

Zeolite is a crystalline hydrated aluminosilicate that may also contain other metals, such as sodium, calcium, barium, and potassium, and that has ion exchange properties (Encarta® World English Dictionary [North American Edition]© & (P) 2001 Microsoft Corporation). Examples of zeolites are ZSM-5, ZSM-11, ZSM-5/ZSM-11 intermediate, ZSM-12, ZSM-21, ZSM-22, ZSM-23, ZSM-35, ZSM-38, ZSM-48, ZSM-50, MCM-22, Zeolite L, Zeolite Beta and Mordenite which are known in the art.

ZSM-5 zeolite is a porous material containing intersecting two-dimensional pore structure with 10-membered oxygen rings. Zeolites with such 10-membered oxygen ring pore structures are often classified as medium-pore zeolites. As used herein, the expression "ZSM-5-type" is meant to refer to those zeolites that are isostructurally the same as ZSM-5 zeolites. Additionally, the expressions "ZSM-5" and "ZSM-5-type" may also be used herein interchangeably to encompass one another and should not be construed in a limiting sense.

ZSM-5 zeolite catalysts and their preparation are described in U.S. Pat. No. 3,702,886, which is herein incorporated by reference. In the present invention, the ZSM-5 zeolite catalyst may include those having a silica/alumina molar ratio of 200 or higher, more particularly from about 250 to about 500 prior to modification. The starting ZSM-5 may be an $NH_4^+$ or $H^+$ form and may contain traces of other cations.

Modification of ZSM-5-type zeolite catalysts with phosphorus-containing compounds has been shown to provide shape selective properties to the catalyst, yielding significantly greater amounts of p-xylene than the thermodynamic equilibrium value when used in toluene methylation compared to unmodified catalysts. Such modification has been shown to provide selectivity for p-xylenes of greater than 80%.

The ZSM-5 may be modified by treating with phosphorus-containing compounds including, but are not limited to, phosphonic, phosphinous, phosphorus and phosphoric acids, salts and esters of such acids and phosphorous halides. In particular, phosphoric acid ($H_3PO_4$) and ammonium hydrogen phosphate (($NH_4$)$_2HPO_4$) may be used as the phosphorus-containing compound to provide a catalyst for toluene methylation with shape selective properties to provide increased p-xylene selectivity. Such modified catalysts may contain phosphorus (P) in an amount of from about 0.01 to about 0.15 g P/g zeolite, more particularly from about 0.02 to about 0.13 g P/g zeolite, and more particularly from about 0.07 g P/g zeolite to about 0.12 g P/g zeolite, and still more particularly from about 0.09 g P/g zeolite to about 0.11 g P/g zeolite. After phosphorus treatment, the phosphorus-treated zeolite may be dried.

The phosphorus-modified ZSM-5 may be made by forming a slurry of a ZSM-5-type zeolite and an aqueous solution of a phosphorus compound and removing water from the slurry to form a phosphorus-modified ZSM-5 zeolite. The phosphorus-modified catalyst prepared as described in Published U.S. Patent Application 20050239635 (STC-03-0006) published Oct. 27, 2005, which is herein incorporated by reference, is not steamed and has a pore volume of from 0.2 ml/g or less.

The phosphorus-modified ZSM-5 may be made by dissolving alumina in a phosphorus-containing acid solution and treating the zeolite with the dissolved alumina solution as described in U.S. Pat. No. 6,943,131 issued Sep. 13, 2005, which is herein incorporated by reference.

The phosphorus-modified ZSM-5 may have particular $^{31}$P MAS NMR peaks indicating the present of free phosphate, phosphate bonded to extra-framework aluminum, or particular phosphate species as described in U.S. Ser. No. 11/136,877 (STC-04-0023) filed May 25, 2005, which is herein incorporated by reference.

Zeolites other than ZSM-5 which are useful in the present invention are medium pore zeolites that have 10 and/or 12 member ring channels system, such as ZSM-4 (Zeolite Omega), ZSM-11, ZSM-12, ZSM-22, ZSM-23, Zeolite Beta, Mordenite, MCM-22 and combinations and mixtures thereof. Silica-alumina phosphates (SAPO), aluminum phosphates (AlPO) and combinations and mixtures thereof are also useful in the present invention.

The phosphorus-modified zeolite may be heated at 300° C. or higher after phosphorus treatment and then combined with an inorganic oxide binder material to form a zeolite-binder mixture which forms a bound zeolite catalyst as described in U.S. Ser. No. 11/195,970 (STC-05-0001) filed Aug. 3, 2005, which is herein incorporated by reference.

In the present invention, the phosphorus-modified zeolite is combined with a binder material which has been treated with a mineral acid or a solution of a mineral acid. The binder material includes inorganic oxide materials, such as alumina, clay, aluminum phosphate and silica-alumina. In particular, a binder of alumina or clay or their combinations is particularly useful.

When used in aromatic alkylation, especially toluene methylation, a bound phosphorus-modified zeolite catalyst which has had the inorganic binder material treated with a mineral acid, such as hydrochloric acid, nitric acid, phosphoric acid or sulfuric acid, before combining the binder material with the phosphorus-modified zeolite will provide increased selectivity to p-xylene. In addition, a phosphorus-modified zeolite catalyst bound with an inorganic binder material which has been treated with a mineral acid will produce toluene methylation product with relatively lower C9+ content. Also, a phosphorus-modified zeolite catalyst bound with an inorganic binder material which has been treated with a mineral acid will be more resistant to catalyst attrition as measured by crush strength.

The inorganic binder material is treated with a mineral acid by adding a sufficient amount of the mineral acid to form a mixture between the inorganic binder material and the liquid mineral acid in which there is no excess liquid.

After forming the mixture between the inorganic binder material and the mineral acid, the phosphorus-modified zeolite is mixed into the mixture and water is added to form a paste which can be extruded to from a shaped catalyst precursor. The catalyst precursor is calcined to form a bound zeolite catalyst at a temperature of 400° C. or higher, more particularly at a temperature between 500° C. and 700° C. Such heating may be carried out for 0.5 hours or more to form the bound catalyst. The bound catalyst may contain from about 1% to about 99% binder by total weight of bound catalyst, more particularly from about 10% to about 50% binder by total weight of bound catalyst.

The bound P-modified zeolite catalyst may be mildly steamed at a temperature of 300° C. or lower before using the catalyst in any reaction. The steaming can be carried out in-situ or ex-situ of the reactor. The use of catalyst steaming at mild temperatures is described in co-pending U.S. patent application Ser. No. 11/122,919 (STC-04-0021), filed May 5, 2005, entitled "Hydrothermal Treatment of Phosphorus-Modified Zeolite Catalysts," which is herein incorporated by reference.

The bound P-modified ZSM-5 catalyst may be contacted with an appropriate feed of an aromatic hydrocarbon and an alkylating agent under alkylation reaction conditions to carry out aromatic alkylation. The catalyst has particular application for use in toluene methylation utilizing a toluene/methanol feed. A gas cofeed may also be used. The cofeed gas may include hydrogen or an inert gas. As used herein, the expression "alkylation feed" is meant to encompass the aromatic compound and the alkylating agent. As used herein, the expression "methylation feed" is meant to encompass the feed of toluene and methanol.

In addition to any cofeed gas, water that may be in the form of steam, may also be introduced into the reactor as cofeed along with the alkylation feed. The water or steam used for the methylation reaction may be introduced with or without hydrogen or inert gas as cofeed with the alkylation feed to the reactor during the start up of the alkylation reaction, or it may be introduced subsequent to initial start up. In either case, liquid water may be added and vaporized prior to its mixing with cofeed gas (if any) and the alkylation feed. The use of water cofeed is described in U.S. Patent App. Publication No. US2005/0070749 A1 (STC-03-0008)), published Mar. 31, 2005, and entitled "Toluene Methylation Process," and in U.S. Ser. No. 11/127,357 (STC-04-0016) filed May 12, 2005, as a continuation-in-part application entitled "Toluene Methylation Process with Increased Methanol Selectivity", both of which are herein incorporated by reference.

The reactor pressure for toluene methylation or other aromatic alkylation may vary, but typically ranges from about 10 to about 1000 psig. Reactor temperatures may vary, but typically range from about 400 to about 700° C. Upon introduction of feed into the reactor, the catalyst bed temperature may be adjusted to a selected reaction temperature to effect a desired conversion. The temperature may be increased gradually at a rate of from about 1° C./min to about 10° C./min to provide the desired final reactor temperature. As used in the examples, reactor temperature refers to the temperature as measured at the inlet of catalyst bed of the reactor.

The catalyst of the claimed invention may be used in a process for toluene methylation with a startup procedure in which the toluene/methanol feed is introduced into the reactor at a relatively high liquid hourly space velocity (LHSV) with a cofeed of hydrogen for one-half to about 20 hours before running the reactor at a relatively lower LHSV as described in U.S. Ser. No. 10/632,254 (STC-03-0004) filed Aug. 1, 2003, which is herein incorporated by reference.

The reaction may be carried out in a variety of different reactors that are commonly used for carrying out aromatic alkylation reactions. Single or multiple reactors in series and/or parallel are suitable for carrying out the aromatic alkylation. Methanol and/or toluene may be added to the product stream entering the second and subsequent reactors when using multiple reactors in series.

The P-modified ZSM-5 zeolite catalyst, as described herein, has particular application for use in toluene methylation for preparing a xylene product from a feed of toluene and methanol. The catalyst provides increased selectivity for p-xylene when used in toluene methylation. In particular, the catalyst may provide greater than 85%, 90% or 95% para-xylene selectivity when used in toluene methylation. Additionally, in certain instances, greater than 95% of total xylene selectivity may be achieved.

Additionally, the bound P/ZSM-5 catalyst described herein will provide steady catalyst activity and selectivity for toluene methylation over the same periods of times under appropriate reaction conditions as unbound P/ZSM-5 catalysts and bound P/ZSM-5 in which the inorganic binder material has not been treated with a mineral acid.

Processes useful for the present invention other than toluene methylation would include aromatic alkylation and transalkylation, toluene disproportionation, methanol to gasoline (MTG) processes and n-paraffin ($C_6$ and higher) cyclization.

The invention having been generally described, the following examples are given as particular embodiments of the invention and to demonstrate the practice and advantages thereof. It is understood that the examples are given by way of illustration and are not intended to limit the specification or the claims to follow in any manner. The following examples serve only to illustrate and not to limit the invention.

As used herein, catalytic activity can be expressed as the % moles of the toluene converted with respect to the moles of toluene fed and can be defined by the following formulas:

$$\text{Mole \% Toluene Conversion} = [(T_i - T_o)/T_i] \times 100 \quad (1)$$

where, $T_i$ is the number of moles of toluene fed and $T_o$ is the number of moles toluene unreacted. As used herein, selectivity for mixed xylenes may be expressed as:

$$\text{Mole \% Mixed Xylene Selectivity} = [X_{tx}/(T_i - T_o)] \times 100 \quad (2)$$

where, $X_{tx}$ is the number of moles of mixed (o-, m- or p-) xylenes in the product.

As used herein, selectivity for p-xylene may be expressed as:

$$\text{Mole \% p-Xylene Selectivity} = (X_p/X_{tx}) \times 100 \quad (3)$$

where, $X_p$ is the number of moles of p-xylene.

As used herein, methanol conversion may be expressed as:

$$\text{Mole \% Methanol Conversion} = [(M_i - M_o)/M_i] \times 100 \quad (4)$$

where, $M_i$ is the number of moles of methanol fed and $M_o$ is the number of moles methanol unreacted.

As used herein, methanol selectivity for toluene methylation may be expressed as:

$$\text{Mole \% Methanol Selectivity} = [X_{tx}/(M_i - M_o)] \times 100 \quad (5)$$

where, $X_{tx}$ is the number of moles of mixed (o-, m- or p-) xylenes, $M_i$ is the number of moles of methanol fed and $M_o$ is the number of moles of unreacted methanol.

Example 1 (Comparative)

Catalyst A

Synthesis of Catalyst A. A binder free P-modified ZSM-5 (P/ZSM-5) was made. The starting zeolite powder was an $NH_4$-ZSM-5 powder having $SiO_2/Al_2O_3$ mole ratio 280. Slurry containing 450.0 g of $NH_4$-ZSM-5 zeolite and 900 ml of water was prepared in a 2-L beaker. The beaker was placed on a hot plate and the zeolite slurry was stirred using a mechanical (overhead) stirrer with 250-300 rpm. The temperature of the slurry was slowly raised to about 80-85° C. at which time phosphoric acid was added slowly. A weighted 205.2 g of phosphoric acid (Aldrich, 85 wt % in aqueous) was added into the beaker. The slurry temperature was further increased to between 95-100° C. and heating was continued until all liquid was evaporated. The phosphoric-acid modified zeolite was calcined in a convection oven in air at the following temperature program: 90° C. to 120° C. for three hours, at 340° C. to 360° C. for three hours and a 520° C. to 530° C. under air for 13 hours. The calcined zeolite was then crushed and sized using 20 and 40 mesh screens for catalytic reaction or sieved through 80 mesh screen for binding it with a suitable binder. The P/ZSM-5 was analyzed for Si, Al and P by XRF method, and for BET surface area and total pore volume by $N_2$ adsorption. As shown in Table 1, the P/ZSM-5 zeolite contained 36.42 wt % Si, 0.27 wt % Al and 9.38 wt % P, and it had BET surface area of 154 $m^2$/g and total pore volume of 0.12 ml/g. The X-ray diffraction pattern for the P/ZSM-5 was recorded on a Phillips (X'Pert model) diffractometer over a range of 5-55° at a scan rate 2° per minute using $CuK_{\alpha 1}$ radiation and results were given in Table 2.

TABLE 1

| Elemental Analysis, wt % | | | $N_2$ Adsorption | |
|---|---|---|---|---|
| Si | Al | P | SA, $m^2$/g | PV, ml/g |
| 36.42 | 0.27 | 9.38 | 154 | 0.12 |

TABLE 2

Powder XRD Intensity*

| d-spacing [A] | Intensity |
| --- | --- |
| 11.11 | 100 |
| 10.02 | 57 |
| 9.73 | 17 |
| 8.04 | 11 |
| 6.69 | 8 |
| 6.54 | 9 |
| 6.34 | 11 |
| 5.97 | 16 |
| 5.70 | 8 |
| 5.56 | 7 |
| 4.01 | 10 |
| 3.93 | 13 |
| 3.85 | 51 |
| 3.74 | 19 |

TABLE 2-continued

Powder XRD Intensity*

| d-spacing [A] | Intensity |
| --- | --- |
| 3.71 | 29 |
| 3.64 | 10 |
| 2.52 | 25 |
| 2.98 | 9 |

*Intensities shown are scaled in arbitrary units so that most intense peak is 100.

Catalyst A was used for toluene methylation reaction. The reaction was carried out in a fixed bed, continuous flow type reactor. A catalyst charge of 5.4 ml (catalyst size: 20-40 mesh) loaded in a SS-316 tube (OD 0.5 inch, ID 0.33 inch) reactor. Catalyst was dried by slowly raising the catalyst bed temperature (about 5° C./min) to 200° C. under hydrogen flow (50 cc/min) for at least one hour. Catalyst was then steamed by introducing water vapor (2.2 mmole/min) with a carrier gas of $H_2$ (459 cc/min) at 200° C. overnight. A premixed toluene and methanol feed (molar ratio about 4.5) was added to the reactor at 200° C. The liquid hourly space velocity (LHSV) (based on methylation feed) was maintained at about 2 $hr^{-1}$ and a cofeed $H_2$ gas was fed and maintained to provide H2/methylation feed molar ratio of about 7-8. In addition, water was added to reactor as cofeed and was vaporized prior to introduction to reactor. The $H_2O$/methylation feed molar ratio was about 0.8 and reactor pressure was about 20 psig. The catalyst bed inlet temperature was increased incrementally to increase toluene conversion. Reactor streams were analyzed to calculate conversion and selectivity. Product streams were analyzed. Conversion and selectivity for toluene methylation reaction over catalyst A are shown in Table 3.

TABLE 3

| | Time on Stream, h | | | | | | |
| --- | --- | --- | --- | --- | --- | --- | --- |
| | 24.10 | 52.60 | 119.60 | 149.77 | 173.60 | 198.13 | 221.60 |
| Catalyst Bed Inlet Temp, ° C. | 452.3 | 487.7 | 495.7 | 530.3 | 529.6 | 531.0 | 533.7 |
| Liquid Product Analysis, wt % | | | | | | | |
| Water | 19.31 | 20.07 | 20.02 | 19.76 | 19.01 | 19.66 | 19.94 |
| Methanol | 0.86 | 0.75 | 0.66 | 0.58 | 0.53 | 0.56 | 0.57 |
| Dimethylether | 0 | 0 | 0 | 0 | 0 | 0 | 0 |
| Benzene | 0 | 0 | 0 | 0 | 0 | 0 | 0 |
| Toluene | 75.92 | 72.39 | 71.11 | 69.70 | 69.60 | 69.09 | 68.88 |
| Ethylbenzene | 0 | 0 | 0 | 0 | 0 | 0 | 0 |
| p-Xylene | 2.95 | 5.51 | 6.79 | 8.51 | 9.27 | 9.08 | 9.08 |
| m-Xylene | 0.35 | 0.49 | 0.56 | 0.62 | 0.68 | 0.67 | 0.67 |
| o-Xylene | 0.38 | 0.46 | 0.48 | 0.49 | 0.52 | 0.51 | 0.50 |
| Ethyltoluenes | 0 | 0.06 | 0.06 | 0 | 0 | 0 | 0 |
| Trimethylbenzenes | 0.22 | 0.28 | 0.32 | 0.34 | 0.39 | 0.37 | 0.37 |
| C10+ | 0 | 0 | 0 | 0 | 0 | 0 | 0 |
| Conversion/Selectivity, mole % | | | | | | | |
| Toluene Conversion | 3.09 | 5.86 | 7.63 | 9.40 | 10.24 | 10.17 | 10.16 |
| Mixed Xylene Selectivity | 94.92 | 95.51 | 96.06 | 97.07 | 96.91 | 96.60 | 97.06 |
| p-Xylene Selectivity | 80.02 | 85.42 | 86.74 | 88.46 | 88.52 | 88.53 | 88.62 |
| Methanol Selectivity | 28.98 | 42.64 | 50.22 | 56.90 | 60.12 | 60.15 | 60.52 |

Example 2 (Comparative)

Catalyst B

Synthesis of Catalyst B. P-modified ZSM-5 (described as catalyst A earlier) was bound with 20 wt % alumina binder. 17.5 g of alumina (pseudobohemite type, available from Alcoa, HiQ-40 grade) was mixed with 70.0 g of P/ZSM-5 zeolite powder (80 mesh). No acid was used with the alumina. Water was sprayed to the alumina and zeolite mixture to form an extrudable paste which was extruded to make 1/16-inch cylindrical shape extrudates. The bound catalyst was calcined in a convection oven in air at a maximum temperature between 510° C. to 530° C. (10 h) using the same temperature profile as described for catalyst A. The catalyst B was crushed and sized using 20 and 40 mesh screens for catalytic test. Using the same test conditions for catalyst A, catalyst B was tested for toluene methylation and results are summarized in Table 4.

TABLE 4

| | Time on Stream, h | | | | | | |
|---|---|---|---|---|---|---|---|
| | 23.77 | 47.27 | 71.27 | 143.77 | 191.52 | 215.27 | 245.77 |
| Catalyst Bed Inlet Temp, ° C. | 452.9 | 475.5 | 486.0 | 496.1 | 499.9 | 508.7 | 507.6 |
| Liquid Product Analysis, wt % | | | | | | | |
| Water | 19.59 | 20.57 | 20.62 | 20.79 | 20.52 | 20.68 | 20.74 |
| Methanol | 0.21 | 0.14 | 0.13 | 0.14 | 0.17 | 0.16 | 0.17 |
| Dimethylether | 0 | 0 | 0 | 0 | 0 | 0 | 0 |
| Benzene | 0 | 0 | 0 | 0 | 0 | 0 | 0 |
| Toluene | 68.72 | 66.49 | 65.78 | 65.26 | 65.64 | 65.33 | 65.19 |
| Ethylbenzene | 0 | 0 | 0 | 0 | 0 | 0 | 0 |
| p-Xylene | 9.23 | 10.67 | 11.32 | 11.70 | 11.56 | 11.70 | 11.73 |
| m-Xylene | 0.85 | 0.89 | 0.92 | 0.92 | 0.89 | 0.90 | 0.89 |
| o-Xylene | 0.62 | 0.57 | 0.56 | 0.54 | 0.54 | 0.55 | 0.55 |
| Ethyltoluenes | 0.16 | 0.13 | 0.12 | 0.11 | 0.11 | 0.10 | 0.10 |
| Trimethylbenzenes | 0.56 | 0.54 | 0.55 | 0.55 | 0.57 | 0.58 | 0.62 |
| C10+ | 0.07 | 0 | 0 | 0 | 0 | 0 | 0 |
| Conversion/Selectivity, mole % | | | | | | | |
| Toluene Conversion | 11.24 | 12.86 | 13.48 | 13.98 | 13.74 | 13.83 | 13.97 |
| Mixed Xylene Selectivity | 94.06 | 95.48 | 95.73 | 96.02 | 95.81 | 95.80 | 95.56 |
| p-Xylene Selectivity | 86.29 | 87.98 | 88.44 | 88.91 | 88.99 | 88.96 | 89.09 |
| Methanol Selectivity | 51.28 | 58.08 | 60.63 | 62.77 | 62.74 | 63.22 | 64.07 |

Example 3

Catalyst C

Synthesis of Catalyst C. Precalcined P-modified ZSM-5 (described as Catalyst A earlier) was bound with 20 wt % alumina binder. 17.5 g of alumina (pseudobohemite type, available from Alcoa, HiQ-40 grade) was mixed with 7.8 g HNO$_3$ (19.9 wt % in aqueous) and then mixed with 70.1 g of P/ZSM-5 zeolite powder (80 mesh). Water was sprayed on the zeolite-alumina mixture to form an extrudable paste which was extruded to make ¹/₁₆-inch cylindrical shape extrudates. The bound catalyst was calcined in a convection oven in air at a maximum temperature between 510° C. to 530° C. (10 h) using the same temperature profile as described for catalyst A. The catalyst C was crushed and sized using 20 and 40 mesh screens for catalytic test. Using the same test conditions for catalyst A, catalyst C was tested for toluene methylation and results are summarized in Table 5.

TABLE 5

| | Time on Stream, h | | | | | | |
|---|---|---|---|---|---|---|---|
| | 23.25 | 54.25 | 119.58 | 143.25 | 167.25 | 191.48 | 215.75 |
| Catalyst Bed Inlet Temp, ° C. | 451.3 | 483.1 | 495.1 | 506.1 | 516.8 | 516.9 | 519.1 |
| Liquid Product Analysis, wt % | | | | | | | |
| Water | 21.46 | 20.53 | 20.76 | 20.85 | 20.98 | 20.85 | 20.99 |
| Methanol | 0.48 | 0.25 | 0.25 | 0.26 | 0.21 | 0.22 | 0.25 |
| Dimethylether | 0 | 0 | 0 | 0 | 0 | 0 | 0 |
| Benzene | 0 | 0 | 0 | 0 | 0 | 0 | 0 |
| Toluene | 67.32 | 66.60 | 66.44 | 66.09 | 65.40 | 65.51 | 65.27 |
| Ethylbenzene | 0 | 0 | 0 | 0 | 0 | 0 | 0 |
| p-Xylene | 8.64 | 10.77 | 10.86 | 11.15 | 11.67 | 11.68 | 11.80 |
| m-Xylene | 0.71 | 0.69 | 0.65 | 0.64 | 0.68 | 0.68 | 0.66 |
| o-Xylene | 0.57 | 0.49 | 0.44 | 0.42 | 0.43 | 0.43 | 0.42 |
| Ethyltoluenes | 0.19 | 0.14 | 0.12 | 0.11 | 0.11 | 0.10 | 0.10 |
| Trimethylbenzenes | 0.55 | 0.54 | 0.49 | 0.49 | 0.52 | 0.51 | 0.50 |
| C10+ | 0.08 | 0 | 0 | 0 | 0 | 0 | 0 |
| Conversion/Selectivity, mole % | | | | | | | |
| Toluene Conversion | 10.78 | 12.51 | 12.57 | 12.87 | 13.11 | 13.33 | 13.38 |
| Mixed Xylene Selectivity | 93.47 | 95.44 | 95.90 | 96.04 | 96.08 | 96.11 | 96.22 |
| p-Xylene Selectivity | 87.14 | 90.14 | 90.89 | 91.34 | 91.32 | 91.27 | 91.58 |
| Methanol Selectivity | 52.19 | 59.57 | 59.89 | 61.44 | 62.04 | 62.67 | 63.97 |

Example 4

Catalyst D

Synthesis of Catalyst D. Precalcined P-modified ZSM-5 (described as Catalyst A earlier) was bound with 20 wt % alumina binder. 17.5 g of alumina (pseudobohemite type, available from Alcoa, HiQ-40 grade) was mixed with 7.8 g HNO$_3$ (40.0 wt % in aqueous) and then mixed with 70.1 g of P/ZSM-5 zeolite powder (80 mesh). Water was sprayed to the zeolite-alumina mixture to form an extrudable paste which was extruded to make 1/16-inch cylindrical shape extrudates. The bound catalyst was calcined in a convection oven in air at a maximum temperature between 510° C. to 530° C. (10 h) using the same temperature profile as described for catalyst A. The catalyst D was crushed and sized using 20 and 40 mesh screens for catalytic test. Using the same test conditions for catalyst A, catalyst D was tested for toluene methylation and results are summarized in Table 6.

TABLE 6

| | Time on Stream, h | | | | | | |
|---|---|---|---|---|---|---|---|
| | 22.88 | 53.63 | 77.63 | 143.63 | 168.05 | 215.88 | 245.63 |
| Catalyst Bed Inlet Temp, ° C. | 451.4 | 482.5 | 504.0 | 515.2 | 532.1 | 531.5 | 530.5 |
| Liquid Product Analysis, wt % | | | | | | | |
| Water | 20.87 | 19.11 | 20.10 | 20.63 | 20.15 | 20.44 | 20.24 |
| Methanol | 0.25 | 0.31 | 0.28 | 0.30 | 0.29 | 0.29 | 0.31 |
| Dimethylether | 0 | 0 | 0 | 0 | 0 | 0 | 0 |
| Benzene | 0 | 0 | 0 | 0 | 0 | 0 | 0 |
| Toluene | 69.46 | 69.22 | 67.81 | 67.48 | 67.40 | 67.29 | 67.47 |
| Ethylbenzene | 0 | 0 | 0 | 0 | 0 | 0 | 0 |
| p-Xylene | 8.31 | 10.16 | 10.63 | 10.47 | 11.04 | 10.85 | 10.86 |
| m-Xylene | 0.37 | 0.42 | 0.42 | 0.42 | 0.43 | 0.43 | 0.43 |
| o-Xylene | 0.29 | 0.31 | 0.30 | 0.28 | 0.28 | 0.28 | 0.28 |
| Ethyltoluenes | 0.15 | 0.12 | 0.10 | 0.08 | 0.07 | 0.08 | 0.07 |
| Trimethylbenzenes | 0.30 | 0.35 | 0.35 | 0.33 | 0.34 | 0.34 | 0.34 |
| C10+ | 0 | 0 | 0 | 0 | 0 | 0 | 0 |
| Conversion/Selectivity, mole % | | | | | | | |
| Toluene Conversion | 9.17 | 11.08 | 11.64 | 11.41 | 11.72 | 11.63 | 11.63 |
| Mixed Xylene Selectivity | 95.89 | 96.52 | 96.77 | 96.95 | 97.14 | 97.03 | 97.09 |
| p-Xylene Selectivity | 92.63 | 93.27 | 93.66 | 93.76 | 93.95 | 93.88 | 93.89 |
| Methanol Selectivity | 45.11 | 55.24 | 57.50 | 57.28 | 59.15 | 58.50 | 59.18 |

Example 5

Catalyst E

Synthesis of Catalyst E. Precalcined P-modified ZSM-5 (described as Catalyst A earlier) was bound with 20 wt % alumina binder. 17.5 g of alumina (pseudobohemite type, available from Alcoa, HiQ-40 grade) was mixed with 7.8 g HNO$_3$ (49.6 wt % in aqueous) and then mixed with 70.0 g of P/ZSM-5 zeolite powder (80 mesh). Water was sprayed to the zeolite-alumina mixture to form an extrudable paste which was extruded to make 1/16-inch cylindrical shape extrudates. The bound catalyst was calcined in a convection oven in air at a maximum temperature between 510° C. to 530° C. (10 h) using the same temperature profile as described for catalyst A. The catalyst E was crushed and sized using 20 and 40 mesh screens for catalytic test. Using the same test conditions for catalyst A, catalyst E was tested for toluene methylation and results are summarized in Table 7.

TABLE 7

| | Time on Stream, h | | | | | | |
|---|---|---|---|---|---|---|---|
| | 23.70 | 53.70 | 77.45 | 143.75 | 167.13 | 173.62 | 191.45 |
| Catalyst Bed Inlet Temp, ° C. | 448.1 | 481.0 | 502.8 | 503.7 | 523.8 | 530.5 | 530.6 |
| Liquid Product Analysis, wt % | | | | | | | |
| Water | 20.73 | 19.54 | 19.90 | 20.64 | 20.42 | 20.70 | 20.74 |
| Methanol | 0.24 | 0.29 | 0.27 | 0.28 | 0.29 | 0.30 | 0.30 |
| Dimethylether | 0 | 0 | 0 | 0 | 0 | 0 | 0 |
| Benzene | 0 | 0 | 0 | 0 | 0 | 0 | 0 |
| Toluene | 69.68 | 69.26 | 67.83 | 67.38 | 67.44 | 67.23 | 67.38 |
| Ethylbenzene | 0 | 0 | 0 | 0 | 0 | 0 | 0 |
| p-Xylene | 8.38 | 9.84 | 10.92 | 10.65 | 10.80 | 10.72 | 10.56 |
| m-Xylene | 0.32 | 0.38 | 0.41 | 0.39 | 0.42 | 0.42 | 0.40 |
| o-Xylene | 0.24 | 0.27 | 0.26 | 0.26 | 0.26 | 0.26 | 0.25 |
| Ethyltoluenes | 0.16 | 0.12 | 0.10 | 0.10 | 0.08 | 0.07 | 0.07 |

TABLE 7-continued

|  | Time on Stream, h | | | | | | |
| --- | --- | --- | --- | --- | --- | --- | --- |
|  | 23.70 | 53.70 | 77.45 | 143.75 | 167.13 | 173.62 | 191.45 |
| Trimethylbenzenes | 0.25 | 0.30 | 0.30 | 0.29 | 0.30 | 0.30 | 0.29 |
| C10+ | 0 | 0 | 0 | 0 | 0 | 0 | 0 |
| Conversion/Selectivity, mole % | | | | | | | |
| Toluene Conversion | 8.85 | 10.50 | 11.83 | 11.53 | 11.45 | 11.37 | 11.14 |
| Mixed Xylene Selectivity | 96.10 | 96.72 | 97.17 | 97.13 | 97.28 | 97.31 | 97.37 |
| p-Xylene Selectivity | 93.67 | 93.87 | 94.19 | 94.25 | 94.10 | 94.08 | 94.19 |
| Methanol Selectivity | 43.34 | 52.29 | 58.23 | 58.46 | 58.09 | 57.73 | 57.06 |

Example 6

Catalyst F

Synthesis of Catalyst F. Precalcined P-modified ZSM-5 (described as catalyst A earlier) was bound with 20 wt % alumina binder. 17.5 g of alumina (pseudobohemite type, available from Alcoa, HiQ-40 grade) was mixed with 7.8 g $HNO_3$ (70.0 wt % in aqueous) and then mixed with 70.1 g of P/ZSM-5 zeolite powder (80 mesh). Water was sprayed to the zeolite-alumina mixture to form an extrudable paste which was extruded to make 1/16-inch cylindrical shape extrudates. The bound catalyst was calcined in a convection oven in air at a maximum temperature between 510° C. to 530° C. (10 h) using the same temperature profile as described for catalyst A. The catalyst F was crushed and sized using 20 and 40 mesh screens for catalytic test. Using the same test conditions for catalyst A, Catalyst F was tested for toluene methylation and results are summarized in Table 8.

Example 7

Catalyst G. An $NH_4$-ZSM-5 zeolite ($SiO_2/Al_2O_3$ mole ratio 280) was treated with $H_3PO_4$ by a wet impregnation method and then heated at a maximum temperature of 550° C. Analyses of the P-treated ZSM-5 zeolite powder are shown in Tables 9 and 10. The P/ZSM-5 showed similar properties to those of Catalyst A. Catalyst G was made using the P/ZSM-5 zeolite powder and 20% alumina binder which had been prepared as follows: 25.0 g of alumina (pseudobohemite type, available from Alcoa, Hi/Q-40 grade) was mixed with 10.7 g $HNO_3$ (70.0 wt % in aqueous) and then mixed with 100.0 g of P-treated zeolite powder (80 mesh). Water was sprayed on the zeolite-alumina mixture to form an extrudable paste which was extruded to make 1/16-inch cylindrical shape extrudates. The extruded catalyst was calcined as described for catalyst A. Using the same test conditions in example 1, Catalyst G was tested for toluene methylation and results are summarized in Table 11.

TABLE 8

|  | Time on Stream, h | | | | | | |
| --- | --- | --- | --- | --- | --- | --- | --- |
|  | 23.05 | 46.80 | 71.30 | 143.30 | 167.32 | 191.30 | 215.05 |
| Catalyst Bed Inlet Temp, ° C. | 454.2 | 475.6 | 495.0 | 505.7 | 517.5 | 516.4 | 516.1 |
| Liquid Product Analysis, wt % | | | | | | | |
| Water | 20.50 | 20.37 | 20.17 | 20.29 | 20.20 | 20.17 | 20.23 |
| Methanol | 0.41 | 0.48 | 0.47 | 0.54 | 0.56 | 0.57 | 0.57 |
| Dimethylether | 0 | 0 | 0 | 0 | 0 | 0 | 0 |
| Benzene | 0 | 0 | 0 | 0 | 0 | 0 | 0 |
| Toluene | 70.88 | 69.90 | 69.60 | 69.88 | 70.17 | 70.14 | 70.08 |
| Ethylbenzene | 0 | 0 | 0 | 0 | 0 | 0 | 0 |
| p-Xylene | 7.50 | 8.55 | 9.02 | 8.59 | 8.38 | 8.41 | 8.41 |
| m-Xylene | 0.21 | 0.22 | 0.24 | 0.24 | 0.24 | 0.24 | 0.24 |
| o-Xylene | 0.17 | 0.17 | 0.18 | 0.18 | 0.18 | 0.18 | 0.18 |
| Ethyltoluenes | 0.14 | 0.12 | 0.10 | 0.08 | 0.07 | 0.07 | 0.07 |
| Trimethylbenzenes | 0.18 | 0.19 | 0.21 | 0.21 | 0.20 | 0.21 | 0.21 |
| C10+ | 0 | 0 | 0 | 0 | 0 | 0 | 0 |
| Conversion/Selectivity, mole % | | | | | | | |
| Toluene Conversion | 7.66 | 8.78 | 9.53 | 8.54 | 8.14 | 8.69 | 8.58 |
| Mixed Xylene Selectivity | 96.53 | 97.08 | 97.32 | 97.23 | 97.33 | 97.43 | 97.36 |
| p-Xylene Selectivity | 95.19 | 95.60 | 95.53 | 95.32 | 95.23 | 95.19 | 95.16 |
| Methanol Selectivity | 41.74 | 48.33 | 52.36 | 50.76 | 48.74 | 51.77 | 50.73 |

TABLE 9

| Elemental Analysis, wt % | | | N$_2$ Adsorption | |
|---|---|---|---|---|
| Si | Al | P | SA, m$^2$/g | PV, ml/g |
| 35.38 | 0.30 | 9.72 | 188 | 0.15 |

TABLE 10

Powder XRD Intensity*

| d-spacing [A] | Intensity |
|---|---|
| 11.08 | 100 |
| 9.99 | 54 |
| 9.89 | 46 |
| 9.70 | 17 |
| 8.01 | 6 |
| 6.54 | 7 |
| 6.33 | 9 |
| 5.98 | 16 |
| 5.70 | 6 |
| 5.55 | 8 |
| 4.25 | 6 |
| 4.00 | 7 |
| 3.84 | 57 |
| 3.80 | 27 |
| 3.71 | 28 |
| 3.64 | 11 |
| 3.53 | 18 |
| 2.98 | 10 |
| 2.78 | 6 |

*Intensities shown are scaled in arbitrary units so that most intense peak is 100.

Examples 8-9

Clay Used as Matrix

Catalysts H-I

Using the P-modified ZSM-5 powder (described as catalyst A) two catalysts were formed using 10% alumina and 10% kaolin clay as binder matrix.

Catalyst H: 8.75 g of alumina (pseudobohemite type, available from Alcoa, HiQ-40 grade) and 8.75 g of kaolin clay (Aldrich) were mixed, and were mixed with 7.8 g HNO$_3$ (19.9 wt % in aqueous) and then mixed with 70.1 g of P/ZSM-5 zeolite powder (80 mesh). Water was sprayed to the zeolite-alumina mixture to form an extrudable paste which was extruded to make 1/16-inch cylindrical shape extrudates. The bound catalyst was calcined in a convection oven in air at a maximum temperature between 510° C. to 530° C. (10 h) using the same temperature profile as described for catalyst A. The catalyst H was crushed and sized using 20 and 40 mesh screens for catalytic test. Using the same test conditions, catalyst H was tested for toluene methylation and results are summarized in Table 12.

Catalyst I. 8.75 g of alumina (pseudobohemite type, available from Alcoa, HiQ-40 grade) and 8.75 g of kaolin clay (Aldrich) were mixed with 7.8 g HNO$_3$ (40.0 wt % in aqueous) and then mixed with 70.1 g of P/ZSM-5 zeolite powder (80 mesh). Water was sprayed to the zeolite-alumina mixture to form an extrudable paste which was extruded to make 1/16-inch cylindrical shape extrudates. The bound catalyst was calcined in a convection oven in air at a maximum temperature between 510° C. to 530° C. (10 h) using the same temperature profile as described for catalyst A. The catalyst I was crushed and sized using 20 and 40 mesh screens for catalytic test. Using the same test conditions in example 1, catalyst I was tested for toluene methylation and results are summarized in Table 13.

TABLE 11

| | Time on Stream, h | | | | | | |
|---|---|---|---|---|---|---|---|
| | 23.42 | 47.08 | 77.42 | 144.08 | 173.42 | 214.88 | 245.75 |
| Catalyst Bed Inlet Temp, ° C. | 463.4 | 463.8 | 487.0 | 501.0 | 511.0 | 511.8 | 509.20 |
| Liquid Product Analysis, wt % | | | | | | | |
| Water | 20.82 | 20.88 | 21.64 | 21.13 | 20.87 | 20.79 | 20.70 |
| Methanol | 0.04 | 0.08 | 0.06 | 0.05 | 0.06 | 0.06 | 0.06 |
| Dimethylether | 0 | 0 | 0 | 0 | 0 | 0 | 0 |
| Benzene | 0 | 0 | 0 | 0 | 0 | 0 | 0 |
| Toluene | 66.97 | 67.20 | 65.19 | 64.61 | 64.51 | 64.68 | 64.60 |
| Ethylbenzene | 0 | 0 | 0 | 0 | 0 | 0 | 0 |
| p-Xylene | 11.49 | 11.14 | 12.39 | 12.84 | 13.80 | 13.71 | 13.86 |
| m-Xylene | 0.24 | 0.24 | 0.27 | 0.29 | 0.30 | 0.30 | 0.31 |
| o-Xylene | 0.14 | 0.14 | 0.15 | 0.15 | 0.16 | 0.16 | 0.16 |
| Ethyltoluenes | 0.17 | 0.16 | 0.15 | 0.14 | 0.13 | 0.13 | 0.13 |
| Trimethylbenzenes | 0.14 | 0.15 | 0.16 | 0.16 | 0.17 | 0.17 | 0.18 |
| C10+ | 0 | 0 | 0 | 0 | 0 | 0 | 0 |
| Conversion/Selectivity, mole % | | | | | | | |
| Toluene Conversion | 12.17 | 11.36 | 13.26 | 14.30 | 14.86 | 14.64 | 14.80 |
| Mixed Xylene Selectivity | 97.84 | 97.64 | 98.04 | 94.74 | 98.25 | 98.24 | 98.20 |
| p-Xylene Selectivity | 96.83 | 96.74 | 96.76 | 96.69 | 96.79 | 96.79 | 96.74 |
| Methanol Selectivity | 54.01 | 51.43 | 59.13 | 62.95 | 66.06 | 65.70 | 65.39 |

TABLE 12

| | Time on Stream, h | | | | | | |
|---|---|---|---|---|---|---|---|
| | 22.75 | 46.68 | 76.93 | 142.77 | 173.85 | 215.48 | 245.53 |
| Catalyst Bed Inlet Temp, ° C. | 452.6 | 475.7 | 506.2 | 518.1 | 521.5 | 523.8 | 523.9 |
| Liquid Product Analysis, wt % | | | | | | | |
| Water | 19.34 | 19.26 | 19.94 | 19.48 | 19.07 | 18.93 | 18.92 |
| Methanol | 0.31 | 0.29 | 0.24 | 0.22 | 0.25 | 0.27 | 0.27 |
| Dimethylether | 0 | 0 | 0 | 0 | 0 | 0 | 0 |
| Benzene | 0 | 0 | 0 | 0 | 0 | 0 | 0 |
| Toluene | 71.33 | 69.61 | 67.30 | 67.38 | 67.64 | 67.68 | 67.62 |
| Ethylbenzene | 0 | 0 | 0 | 0 | 0 | 0 | 0 |
| p-Xylene | 8.13 | 9.92 | 11.62 | 12.00 | 12.13 | 12.21 | 12.27 |
| m-Xylene | 0.29 | 0.32 | 0.35 | 0.36 | 0.36 | 0.36 | 0.36 |
| o-Xylene | 0.23 | 0.22 | 0.21 | 0.21 | 0.21 | 0.21 | 0.22 |
| Ethyltoluenes | 0.15 | 0.12 | 0.10 | 0.10 | 0.09 | 0.09 | 0.09 |
| Trimethylbenzenes | 0.22 | 0.24 | 0.25 | 0.25 | 0.25 | 0.25 | 0.26 |
| C10+ | 0 | 0 | 0 | 0 | 0 | 0 | 0 |
| Conversion/Selectivity, mole % | | | | | | | |
| Toluene Conversion | 8.73 | 10.60 | 12.63 | 12.86 | 12.88 | 12.89 | 12.90 |
| Mixed Xylene Selectivity | 96.51 | 97.18 | 97.66 | 97.75 | 97.78 | 97.80 | 97.79 |
| p-Xylene Selectivity | 94.04 | 94.76 | 95.37 | 95.43 | 95.54 | 95.52 | 95.48 |
| Methanol Selectivity | 42.93 | 51.87 | 60.22 | 60.41 | 63.03 | 62.30 | 63.05 |

TABLE 13

| | Time on Stream, h | | | | | | |
|---|---|---|---|---|---|---|---|
| | 29.23 | 53.40 | 77.40 | 149.40 | 191.23 | 215.15 | 245.40 |
| Catalyst Bed Inlet Temp, ° C. | 464.5 | 483.9 | 505.3 | 517.2 | 530.9 | 531.7 | 531.2 |
| Liquid Product Analysis, wt % | | | | | | | |
| Water | 21.06 | 19.90 | 20.70 | 19.67 | 19.42 | 19.94 | 19.14 |
| Methanol | 0.27 | 0.30 | 0.32 | 0.38 | 0.35 | 0.36 | 0.38 |
| Dimethylether | 0 | 0 | 0 | 0 | 0 | 0 | 0 |
| Benzene | 0 | 0 | 0 | 0 | 0 | 0 | 0 |
| Toluene | 68.73 | 68.98 | 68.01 | 69.33 | 69.66 | 69.30 | 70.33 |
| Ethylbenzene | 0 | 0 | 0 | 0 | 0 | 0 | 0 |
| p-Xylene | 9.14 | 9.97 | 10.12 | 9.81 | 9.80 | 9.65 | 9.34 |
| m-Xylene | 0.27 | 0.30 | 0.30 | 0.31 | 0.30 | 0.28 | 0.29 |
| o-Xylene | 0.19 | 0.20 | 0.20 | 0.20 | 0.19 | 0.19 | 0.19 |
| Ethyltoluenes | 0.13 | 0.11 | 0.10 | 0.07 | 0.06 | 0.06 | 0.06 |
| Trimethylbenzenes | 0.21 | 0.24 | 0.24 | 0.23 | 0.22 | 0.22 | 0.22 |
| C10+ | 0 | 0 | 0 | 0 | 0 | 0 | 0 |
| Conversion/Selectivity, mole % | | | | | | | |
| Toluene Conversion | 9.72 | 10.58 | 10.56 | 10.06 | 9.82 | 9.67 | 9.30 |
| Mixed Xylene Selectivity | 97.11 | 97.27 | 97.41 | 97.58 | 97.71 | 97.69 | 97.67 |
| p-Xylene Selectivity | 95.19 | 95.24 | 95.26 | 95.14 | 95.22 | 95.35 | 95.12 |
| Methanol Selectivity | 48.49 | 52.69 | 53.99 | 54.01 | 52.76 | 52.57 | 51.01 |

Examples 10-12

Catalyst Made by Alumina Digestion Method

Catalysts J-L

A P-modified ZSM-5 was made by following method described in U.S. Pat. No. 6,943,131 (Ghosh et al., 2005). 5.0 g alumina (pseudobohemite type, available from Alcoa, HiQ-40 grade) was dissolved in 100 ml water and 67.04 g $H_3PO_4$ (85 wt % in aqueous) at temperature 70-80° C. The alumina solution was added to a zeolite slurry containing 250.0 g $NH_4ZSM$-5 ($SiO_2/Al_2O_3$ molar ratio 280) and 500 ml water at temperature 90-100° C. The zeolite slurry was stirred and was evaporated to dryness and the modified ZSM-5 was calcined using the temperature profile described for catalyst A in preceding section. As described below, three catalysts were made by using the P-modified ZSM-5.

Example 10 (Comparative)

Catalyst J—The P-modified ZSM-5 (described above) was bound with 20 wt % alumina binder. 17.5 g of alumina (pseudobohemite type, available from Alcoa, HiQ-40 grade) was mixed with 70.1 g of P/ZSM-5 zeolite powder (80 mesh). No acid was used with the alumina. Water was sprayed to the alumina and zeolite mixture to form an extrudable paste which was extruded to make 1/16-inch cylindrical shape extrudates. The bound catalyst was calcined in a convection oven in air at a maximum temperature between 510° C. to 530° C. (10 h) using the same temperature profile as described for catalyst A. The catalyst J was crushed and sized using 20 and 40 mesh screens for catalytic test. Using the same test conditions in example 1, Catalyst J was tested for toluene methylation and results are summarized in Table 14.

Example 11

Catalyst K—Precalcined P-modified ZSM-5 (described above) was bound with 20 wt % alumina binder. 16.34 g of alumina (pseudobohemite type, available from Alcoa, HiQ-40 grade) was mixed with 7.27 g HNO$_3$ (40.0 wt % in aqueous) and then mixed with 65.4 g of P/ZSM-5 zeolite powder (80 mesh). Water was sprayed to the zeolite-alumina mixture to form an extrudable paste which was extruded to make ¹/₁₆-inch cylindrical shape extrudates. The bound catalyst was calcined in a convection oven in air at a maximum temperature between 510° C. to 530° C. (10 h) using the same temperature profile as described for catalyst A. The catalyst K was crushed and sized using 20 and 40 mesh screens for catalytic test. Using the same test conditions in example 1, catalyst K was tested for toluene methylation and results are summarized in Table 15.

Example 12

Catalyst L. 37.8 g of alumina was mixed with 16.7 g HNO$_3$ (70.0 wt % in aqueous) and then mixed with 151.1 g of the modified ZSM-5 zeolite powder (80 mesh). Water was sprayed to the zeolite-alumina mixture to form an extrudable paste which was extruded to make ¹/₁₆-inch cylindrical shape extrudates. The bound catalyst was calcined in a convection oven in air at a maximum temperature between 510° C. to 530° C. using the same temperature profile as described for catalyst A. The catalyst L was crushed and sized using 20 and 40 mesh screens for catalytic test. Using the same test conditions in example 1, catalyst L was tested for toluene methylation and results are summarized in Table 16.

TABLE 14

|  | Time on Stream, h | | | | | | |
| --- | --- | --- | --- | --- | --- | --- | --- |
|  | 23.50 | 47.48 | 77.83 | 167.52 | 191.52 | 215.45 | 239.43 |
| Catalyst Bed Inlet Temp, ° C. | 456.2 | 478.0 | 488.5 | 489.1 | 489.3 | 489.3 | 489.2 |
| Liquid Product Analysis, wt % | | | | | | | |
| Water | 20.06 | 20.10 | 19.97 | 20.07 | 19.82 | 19.94 | 19.74 |
| Methanol | 0.02 | 0 | 0 | 0 | 0 | 0 | 0 |
| Dimethylether | 0 | 0 | 0 | 0 | 0 | 0 | 0 |
| Benzene | 0 | 0 | 0 | 0 | 0 | 0 | 0 |
| Toluene | 68.09 | 66.78 | 66.20 | 65.76 | 65.79 | 65.63 | 65.74 |
| Ethylbenzene | 0 | 0 | 0 | 0 | 0 | 0 | 0 |
| p-Xylene | 9.01 | 10.23 | 10.80 | 11.05 | 11.23 | 11.31 | 11.39 |
| m-Xylene | 1.23 | 1.47 | 1.59 | 1.63 | 1.63 | 1.63 | 1.63 |
| o-Xylene | 0.75 | 0.71 | 0.74 | 0.77 | 0.77 | 0.77 | 0.77 |
| Ethyltoluenes | 0.19 | 0.16 | 0.15 | 0.14 | 0.13 | 0.13 | 0.13 |
| Trimethylbenzenes | 0.59 | 0.55 | 0.56 | 0.58 | 0.59 | 0.59 | 0.60 |
| C10+ | 0.06 | 0 | 0 | 0 | 0 | 0 | 0 |
| Conversion/Selectivity, mole % | | | | | | | |
| Toluene Conversion | 11.94 | 13.29 | 13.97 | 14.47 | 14.66 | 14.68 | 14.82 |
| Mixed Xylene Selectivity | 94.01 | 95.40 | 95.68 | 95.68 | 95.74 | 95.74 | 95.75 |
| p-Xylene Selectivity | 82.03 | 82.44 | 82.24 | 82.17 | 82.48 | 82.51 | 82.60 |
| Methanol Selectivity | 51.13 | 57.39 | 60.57 | 62.64 | 63.36 | 63.65 | 64.04 |

TABLE 15

|  | Time on Stream, h | | | | | |
| --- | --- | --- | --- | --- | --- | --- |
|  | 23.10 | 47.10 | 77.90 | 143.65 | 167.55 | 191.90 |
| Catalyst Bed Inlet Temp, ° C. | 452.1 | 464.8 | 478.8 | 481.0 | 481.6 | 481.6 |
| Liquid Product Analysis, wt % | | | | | | |
| Water | 19.69 | 19.54 | 20.06 | 19.54 | 19.76 | 20.31 |
| Methanol | 0.03 | 0 | 0 | 0 | 0.01 | 0.01 |
| Dimethylether | 0 | 0 | 0 | 0 | 0 | 0 |
| Benzene | 0 | 0 | 0 | 0 | 0 | 0 |
| Toluene | 68.23 | 67.50 | 66.03 | 66.37 | 66.16 | 65.44 |
| Ethylbenzene | 0 | 0 | 0 | 0 | 0 | 0 |
| p-Xylene | 9.84 | 10.61 | 11.53 | 11.69 | 11.70 | 11.88 |
| m-Xylene | 0.96 | 1.11 | 1.16 | 1.17 | 1.15 | 1.14 |
| o-Xylene | 0.56 | 0.57 | 0.57 | 0.58 | 0.57 | 0.57 |
| Ethyltoluenes | 0.18 | 0.18 | 0.15 | 0.15 | 0.15 | 0.14 |
| Trimethylbenzenes | 0.52 | 0.49 | 0.50 | 0.51 | 0.51 | 0.51 |
| C10+ | 0 | 0 | 0 | 0 | 0 | 0 |
| Conversion/Selectivity, mole % | | | | | | |
| Toluene Conversion | 12.09 | 13.04 | 14.15 | 14.31 | 14.32 | 14.69 |
| Mixed Xylene Selectivity | 95.07 | 95.59 | 96.04 | 96.07 | 96.09 | 96.17 |
| p-Xylene Selectivity | 86.64 | 86.34 | 86.96 | 87.00 | 87.21 | 87.44 |
| Methanol Selectivity | 52.80 | 56.57 | 61.59 | 61.76 | 61.93 | 63.38 |

TABLE 16

| | Time on Stream, h | | | | | | |
|---|---|---|---|---|---|---|---|
| | 24.85 | 47.53 | 120.12 | 143.85 | 167.53 | 191.53 | 222.35 |
| Catalyst Bed Inlet Temp, ° C. | 446.2 | 473.6 | 494.6 | 505.0 | 505.4 | 505.6 | 505.0 |
| Product Analysis, wt % | | | | | | | |
| Water | 19.97 | 19.74 | 20.11 | 19.80 | 19.85 | 20.03 | 20.11 |
| Methanol | 0.17 | 0.13 | 0.12 | 0.11 | 0.12 | 0.12 | 0.12 |
| Dimethylether | 0 | 0 | 0 | 0 | 0 | 0 | 0 |
| Benzene | 0 | 0 | 0 | 0 | 0 | 0 | 0 |
| Toluene | 70.41 | 68.17 | 66.63 | 66.36 | 66.23 | 65.82 | 65.53 |
| Ethylbenzene | 0 | 0 | 0 | 0 | 0 | 0 | 0 |
| p-Xylene | 8.49 | 11.00 | 12.15 | 12.71 | 12.78 | 12.99 | 13.18 |
| m-Xylene | 0.32 | 0.36 | 0.39 | 0.40 | 0.41 | 0.41 | 0.43 |
| o-Xylene | 0.24 | 0.23 | 0.23 | 0.23 | 0.23 | 0.23 | 0.24 |
| Ethyltoluenes | 0.17 | 0.14 | 0.12 | 0.11 | 0.11 | 0.11 | 0.12 |
| Trimethylbenzenes | 0.24 | 0.25 | 0.26 | 0.27 | 0.27 | 0.27 | 0.28 |
| C10+ | 0 | 0 | 0 | 0 | 0 | 0 | 0 |
| Conversion/Selectivity, mole % | | | | | | | |
| Toluene Conversion | 9.42 | 12.10 | 13.41 | 14.08 | 14.06 | 14.32 | 14.62 |
| Mixed Xylene Selectivity | 96.36 | 97.27 | 97.55 | 97.67 | 97.68 | 97.67 | 97.64 |
| p-Xylene Selectivity | 93.84 | 94.97 | 95.18 | 95.27 | 95.28 | 95.27 | 95.20 |
| Methanol Selectivity | 44.34 | 56.00 | 61.54 | 64.33 | 64.82 | 65.73 | 64.99 |

TABLE 17

PX Selectivity Over Various P-ZSM-5 Catalysts

| Catalyst | Binder | g HNO3/g Binder[a] | PX Selectivity (mole %) |
|---|---|---|---|
| A | No binder | | 88.53 |
| B | 20% Al$_2$O$_3$ | 0 | 88.91 |
| C | 20% Al$_2$O$_3$ | 0.089 | 91.58 |
| D | 20% Al$_2$O$_3$ | 0.178 | 93.84 |
| E | 20% Al$_2$O$_3$ | 0.220 | 94.15 |
| F | 20% Al$_2$O$_3$ | 0.311 | 95.19 |
| G | 20% Al$_2$O$_3$ | 0.311 | 96.76 |
| H | 10% Al$_2$O$_3$ (+10% Kaolin) | 0.089 | 95.16 |
| I | 10% Al$_2$O$_3$ (+10% Kaolin) | 0.178 | 95.22 |
| J[b] | 20% Al$_2$O$_3$ | 0 | 82.41 |
| K[b] | 20% Al$_2$O$_3$ | 0.178 | 87.20 |
| L[b] | 20% Al$_2$O$_3$ | 0.311 | 95.28 |

[a]Binder or binder plus kaolin;
[b]PZSM-5 made by Al digestion method

Examples 13-16 (Comparative)

Catalysts M-N

Synthesis of Catalysts M-N. Zeolite H-ZSM-5 (SiO$_2$/Al$_2$O$_3$ molar ratio 280) powder was bound with alumina to make two catalysts—one without mixing alumina with nitric acid and the other with mixing alumina with nitric acid. The zeolites were not modified with phosphorus.

Example 13

Catalyst M: 25.0 g of alumina (pseudobohemite type, available from Alcoa, HiQ-40 grade) was mixed with 100.1 g of the HZSM-5 zeolite powder (80 mesh). Water was sprayed to the alumina and zeolite mixture which was extruded to make 1/16-inch cylindrical shape extrudates.

Example 14

Catalyst N: 20.2 g of alumina (pseudobohemite type, available from Alcoa, HiQ-40 grade) was mixed with 8.97 g HNO$_3$ (70.0 wt % in aqueous) and then mixed with 80.6 g of the HZSM-5 zeolite powder (80 mesh). Water was sprayed to the zeolite-alumina mixture to form an extrudable paste which was extruded to make 1/16-inch cylindrical shape extrudates.

Both extruded catalysts were calcined in a convection oven in air at a maximum temperature between 510° C. to 530° C. (10 h) using the same temperature profile as described for catalyst A. The catalysts were crushed and sized using 20 and 40 mesh screens for catalytic test. Using the same test conditions in example 1, Catalysts M and N were tested for toluene methylation and results are summarized in Tables 18 and 19, respectively.

TABLE 18

| | Time on Stream, h | | | | | | |
|---|---|---|---|---|---|---|---|
| | 23.32 | 47.33 | 77.87 | 143.28 | 173.88 | 198.08 | 245.57 |
| Catalyst Bed Inlet Temp, ° C. | 453.7 | 464.4 | 463.7 | 474.9 | 472.5 | 473.2 | 472.5 |
| Liquid Product Analysis, wt % | | | | | | | |
| Water | 20.28 | 19.86 | 20.11 | 20.18 | 20.00 | 19.68 | 20.03 |
| Methanol | 0 | 0 | 0 | 0 | 0 | 0 | 0 |
| Dimethylether | 0 | 0 | 0 | 0 | 0 | 0 | 0 |
| Benzene | 0 | 0.16 | 0.12 | 0.13 | 0.10 | 0.09 | 0.08 |
| Toluene | 66.00 | 66.03 | 65.83 | 65.75 | 66.01 | 66.47 | 66.21 |
| Ethylbenzene | 0 | 0 | 0 | 0 | 0 | 0 | 0 |

TABLE 18-continued

|  | Time on Stream, h | | | | | | |
|---|---|---|---|---|---|---|---|
|  | 23.32 | 47.33 | 77.87 | 143.28 | 173.88 | 198.08 | 245.57 |
| p-Xylene | 3.07 | 3.23 | 3.34 | 3.42 | 3.56 | 3.58 | 3.68 |
| m-Xylene | 6.47 | 6.59 | 6.43 | 6.43 | 6.22 | 6.11 | 5.99 |
| o-Xylene | 2.68 | 2.74 | 2.71 | 2.72 | 2.64 | 2.61 | 2.56 |
| Ethyltoluenes | 0.74 | 0.55 | 0.47 | 0.36 | 0.36 | 0.33 | 0.33 |
| Trimethylbenzenes | 0.66 | 0.74 | 0.86 | 0.91 | 0.97 | 0.98 | 0.99 |
| C10+ | 0.11 | 0.11 | 0.13 | 0.12 | 0.14 | 0.14 | 0.14 |
| Conversion/Selectivity, mole % | | | | | | | |
| Toluene Conversion | 13.70 | 14.05 | 14.08 | 14.26 | 13.86 | 13.74 | 13.68 |
| Mixed Xylene Selectivity | 90.02 | 89.53 | 89.36 | 89.87 | 90.07 | 89.67 | 90.18 |
| p-Xylene Selectivity | 25.13 | 25.70 | 26.74 | 27.20 | 28.64 | 29.14 | 30.10 |
| Methanol Selectivity | 55.25 | 56.46 | 56.88 | 57.81 | 56.57 | 55.94 | 55.88 |

TABLE 19

|  | Time on Stream, h | | | | | | |
|---|---|---|---|---|---|---|---|
|  | 23.23 | 47.48 | 71.23 | 142.98 | 173.23 | 197.23 | 244.55 |
| Catalyst Bed Inlet Temp, ° C. | 449.9 | 441.2 | 440.1 | 442.5 | 453.7 | 460.3 | 469.2 |
| Liquid Product Analysis, wt % | | | | | | | |
| Water | 20.60 | 21.23 | 21.00 | 21.26 | 20.91 | 19.52 | 19.65 |
| Methanol | 0 | 0 | 0 | 0 | 0 | 0 | 0 |
| Dimethylether | 0 | 0 | 0 | 0 | 0 | 0 | 0 |
| Benzene | 0.23 | 0.12 | 0.10 | 0.08 | 0.09 | 0.10 | 0.10 |
| Toluene | 64.02 | 64.68 | 65.05 | 65.08 | 65.22 | 66.02 | 65.80 |
| Ethylbenzene | 0 | 0 | 0 | 0 | 0 | 0 | 0 |
| p-Xylene | 3.38 | 3.17 | 3.22 | 3.41 | 3.46 | 3.65 | 3.69 |
| m-Xylene | 7.22 | 6.49 | 6.37 | 6.07 | 6.20 | 6.50 | 6.59 |
| o-Xylene | 3.03 | 2.70 | 2.65 | 2.55 | 2.61 | 2.72 | 2.75 |
| Ethyltoluenes | 0.71 | 0.76 | 0.73 | 0.58 | 0.50 | 0.43 | 0.39 |
| Trimethylbenzenes | 0.71 | 0.73 | 0.76 | 0.85 | 0.90 | 0.93 | 0.92 |
| C10+ | 0.11 | 0.11 | 0.11 | 0.12 | 0.12 | 0.13 | 0.11 |
| Conversion/Selectivity, mole % | | | | | | | |
| Toluene Conversion | 15.36 | 14.25 | 14.05 | 13.29 | 13.40 | 14.31 | 14.01 |
| Mixed Xylene Selectivity | 88.47 | 88.26 | 88.67 | 88.42 | 89.41 | 89.72 | 90.67 |
| p-Xylene Selectivity | 24.81 | 25.66 | 26.30 | 28.36 | 28.20 | 28.35 | 28.32 |
| Methanol Selectivity | 60.32 | 55.75 | 55.58 | 52.29 | 53.87 | 57.24 | 56.56 |

Catalysts O-P

Synthesis of Catalysts O and P. Zeolite NH$_4$-ZSM-5 (SiO$_2$/Al$_2$O$_3$ molar ratio 700) powder was bound with alumina to make two catalysts—one without mixing alumina with nitric acid and the other with mixing alumina. The zeolites were not modified with phosphorus.

Example 15

Catalyst O: 17.5 g of alumina (pseudobohemite type, available from Alcoa, HiQ-40 grade) was mixed with 70.0 g of the NH$_4$ZSM-5 zeolite powder (80 mesh). Water was sprayed to the alumina and zeolite mixture and was extruded to make 1/16-inch cylindrical shape extrudates.

Example 16

Catalyst P: 17.5 g of alumina (pseudobohemite type, available from Alcoa, HiQ-40 grade) was mixed with 7.79 g HNO$_3$ (70.0 wt % in aqueous) and then mixed with 70.1 g of the NH$_4$ZSM-5 zeolite powder (80 mesh). Water was sprayed to the zeolite-alumina mixture to form an extrudable paste which was extruded to make 1/16-inch cylindrical shape extrudates.

Both extruded catalysts were calcined in a convection oven in air at a maximum temperature between 510° C. to 530° C. (10 h) using the same temperature profile as described for catalyst A. The catalysts were crushed and sized using 20 and 40 mesh screens for catalytic test. Using the same test conditions in example 1, Catalysts O and P were tested for toluene methylation and results are summarized in Tables 20 & 21 respectively.

TABLE 20

| | Time on Stream, h | | | | | | |
|---|---|---|---|---|---|---|---|
| | 23.58 | 53.58 | 119.58 | 143.58 | 173.58 | 197.83 | 221.58 |
| Catalyst Bed Inlet Temp, ° C. | 446.9 | 479.10 | 483.9 | 495.1 | 497.6 | 494.4 | 494.4 |
| Product Analysis, wt % | | | | | | | |
| Water | 21.15 | 20.35 | 21.01 | 20.60 | 19.62 | 20.37 | 20.33 |
| Methanol | 0 | 0 | 0 | 0 | 0 | 0 | 0 |
| Dimethylether | 0 | 0 | 0 | 0 | 0 | 0 | 0 |
| Benzene | 0 | 0.05 | 0.05 | 0.05 | 0.05 | 0 | 0.05 |
| Toluene | 66.11 | 65.62 | 65.08 | 64.97 | 65.72 | 64.94 | 65.09 |
| Ethylbenzene | 0 | 0 | 0 | 0 | 0 | 0 | 0 |
| p-Xylene | 5.62 | 5.80 | 6.15 | 6.51 | 7.06 | 7.43 | 7.47 |
| m-Xylene | 4.16 | 4.80 | 4.57 | 4.72 | 4.56 | 4.32 | 4.23 |
| o-Xylene | 1.77 | 2.12 | 2.02 | 2.04 | 1.96 | 1.88 | 1.82 |
| Ethyltoluenes | 0.32 | 0.11 | 0.08 | 0.07 | 0.07 | 0.07 | 0.07 |
| Trimethylbenzenes | 0.77 | 0.94 | 0.93 | 0.91 | 0.91 | 0.90 | 0.86 |
| C10+ | 0.10 | 0.11 | 0.10 | 0.09 | 0.09 | 0.08 | 0.07 |
| Conversion/Selectivity, mole % | | | | | | | |
| Toluene Conversion | 12.62 | 13.78 | 13.85 | 14.28 | 14.47 | 14.56 | 14.42 |
| Mixed Xylene Selectivity | 91.98 | 91.95 | 92.74 | 93.07 | 93.37 | 93.87 | 93.63 |
| p-Xylene Selectivity | 48.68 | 45.55 | 48.23 | 49.05 | 52.12 | 54.50 | 55.25 |
| Methanol Selectivity | 51.59 | 56.85 | 57.64 | 59.64 | 60.84 | 61.57 | 60.82 |

TABLE 21

| | Time on Stream, h | | | | | | |
|---|---|---|---|---|---|---|---|
| | 24.38 | 52.88 | 119.88 | 143.22 | 173.88 | 198.02 | 221.88 |
| Catalyst Bed Inlet Temp, ° C. | 449.2 | 495.7 | 502.7 | 503.3 | 495.7 | 496.7 | 500.7 |
| Product Analysis, wt % | | | | | | | |
| Water | 20.20 | 18.40 | 20.24 | 20.17 | 21.11 | 17.95 | 20.86 |
| Methanol | 0 | 0 | 0 | 0 | 0 | 0 | 0 |
| Dimethylether | 0 | 0 | 0 | 0 | 0 | 0 | 0 |
| Benzene | 0 | 0.06 | 0.06 | 0 | 0 | 0 | 0 |
| Toluene | 66.44 | 66.31 | 64.95 | 64.71 | 64.74 | 65.98 | 64.28 |
| Ethylbenzene | 0 | 0 | 0 | 0 | 0 | 0 | 0 |
| p-Xylene | 5.31 | 6.13 | 6.25 | 7.03 | 7.35 | 7.93 | 7.45 |
| m-Xylene | 4.84 | 5.43 | 5.01 | 4.73 | 4.41 | 4.59 | 4.19 |
| o-Xylene | 1.99 | 2.34 | 2.21 | 2.14 | 2.08 | 2.17 | 1.97 |
| Ethyltoluenes | 0.31 | 0.18 | 0.14 | 0.08 | 0.08 | 0.09 | 0.08 |
| Trimethylbenzenes | 0.81 | 1.03 | 1.03 | 1.04 | 1.09 | 1.17 | 1.07 |
| C10+ | 0.10 | 0.12 | 0.11 | 0.11 | 0.12 | 0.13 | 0.11 |
| Conversion/Selectivity, mole % | | | | | | | |
| Toluene Conversion | 13.02 | 14.71 | 14.57 | 14.99 | 14.16 | 15.51 | 14.76 |
| Mixed Xylene Selectivity | 92.24 | 91.95 | 92.08 | 93.06 | 98.19 | 92.60 | 92.69 |
| p-Xylene Selectivity | 43.70 | 44.13 | 46.39 | 50.59 | 53.09 | 54.00 | 54.75 |
| Methanol Selectivity | 53.55 | 60.41 | 60.08 | 62.45 | 62.82 | 63.98 | 61.08 |

Figure 2:
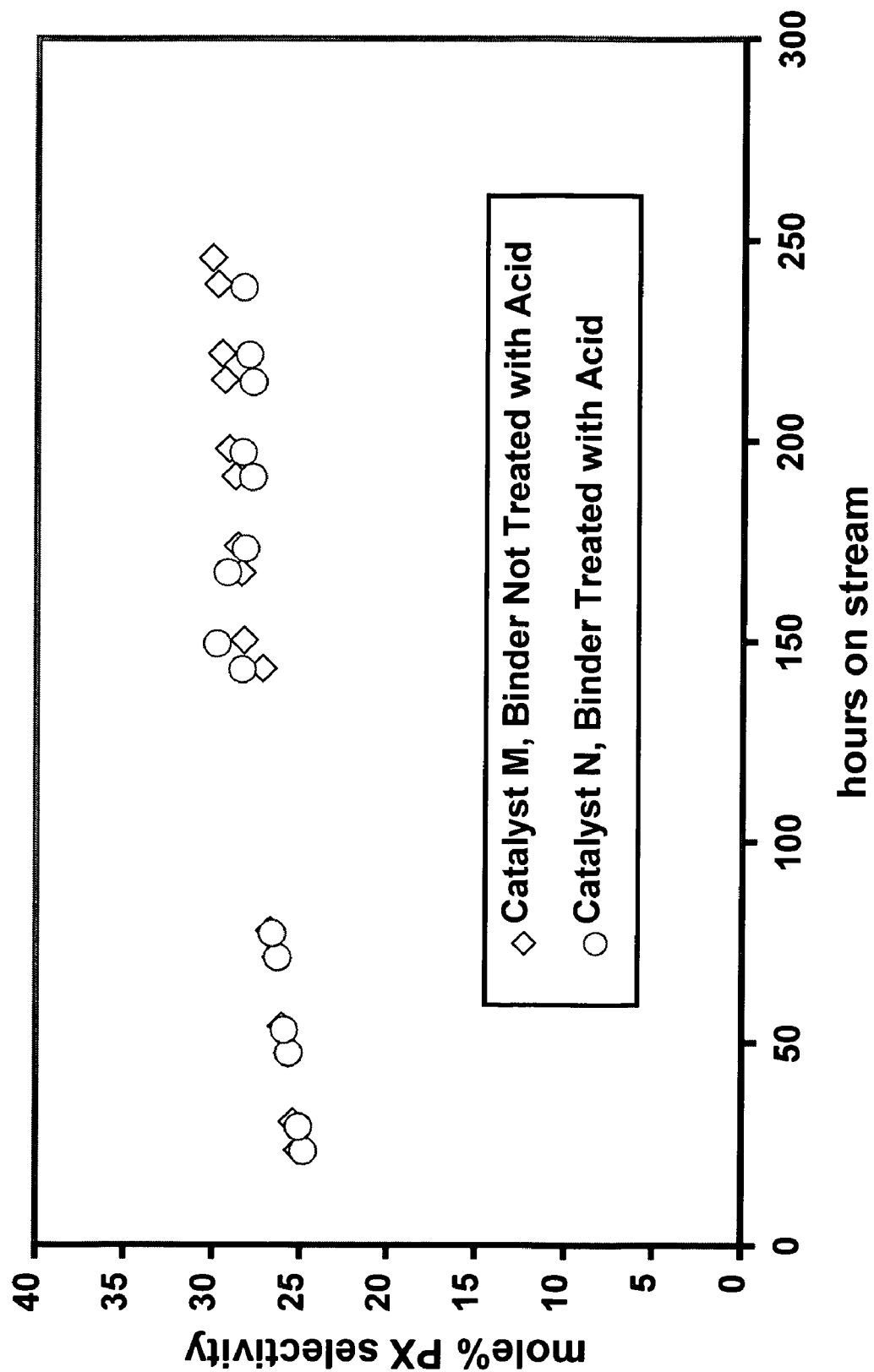
FIG. 2 is a plot of p-xylene selectivity as a function of time on stream for the toluene methylation reaction for catalysts M of Example 13 and catalyst N of Example 14.

As shown in the data above, the combination of a phosphorus-modified ZSM-5 with alumina or clay binder material which has been treated with nitric acid in a catalyst for a process of methylation of toluene results in improved selectivity to p-xylene. The comparative examples without binder (Example 1), without treatment of the binder with mineral acid (Examples 2 and 10), without phosphorus modification of the zeolite (Examples 13-16) show lower selectivity to p-xylene than a catalyst of a phosphorus-modified ZSM-5 with alumina or clay binder material which has been treated with nitric acid (Examples 3-9, 11 and 12). FIG. 1 shows the difference in p-xylene selectivity for a bound P-modified ZSM-5 without (Example 2, Catalyst B) and with (Example 6, Catalyst F) treatment of the binder with mineral acid. FIG. 2 shows the lack of effect on p-xylene selectivity for a bound ZSM-5 without phosphorus modification and without (Example 13, Catalyst M) and with (Example 14, Catalyst N) treatment of the binder with mineral acid.

The crush strength using a flat plate method was measured for calcined 1/16-inch extrudates of Catalyst B (Example 2 Comparative without acid treatment of the binder), Catalyst C, Catalyst D and Catalyst F (Examples 3, 4 and 6 with acid treatment of the binder). The average crush strength is shown in Table 22.

TABLE 22

| Catalyst | Average Crush Strength (lb/mm) |
|---|---|
| B | 2.10 |
| C | 3.36 |
| D | 3.41 |
| F | 3.68 |

As shown in the data above, the combination of a phosphorus-modified ZSM-5 with alumina or clay binder material which has been treated with nitric acid results in improved crush strength. The comparative example of a phosphorus-modified ZSM-5 with alumina binder material which has not been treated with nitric acid (Catalyst B) shows lower average crush strength than P-ZSM-5 catalysts having alumina binder material which has been treated with nitric acid (Catalysts C, D and F). Higher crush strength indicates that such catalyst should have less physical attrition of the catalyst and longer catalyst life in process conditions.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter of Patent of the United States of America is:

1. A method of preparing a zeolite catalyst comprising:
   a) treating a zeolite with a phosphorus compound to form a phosphorus-treated zeolite;
   b) treating an inorganic oxide binder material with a mineral acid;
   c) combining the phosphorus-treated zeolite with the treated inorganic oxide binder material to form a zeolite-binder mixture; and
   d) heating the zeolite-binder mixture at temperature of about 4000° C. or higher to form a bound zeolite catalyst.

2. The method of claim 1, wherein the binder material includes at least one of alumina, clay, aluminum phosphate or silica-alumina.

3. The method of claim 1, wherein the binder material is an alumina-containing material.

4. The method of claim 1 wherein the binder material is present in an amount of from about 1% to about 99% by weight of the bound zeolite catalyst.

5. The method of claim 1, wherein the binder material contains from about 1% to 99% by weight alumina.

6. The method of claim 1, wherein the mineral acid is hydrochloric acid, nitric acid, phosphoric acid or sulfuric acid.

7. The method of claim 1, wherein the mineral acid is nitric acid.

8. The method of claim 1, wherein the zeolite contains 10-oxygen ring pores.

9. The method of claim 1, wherein the zeolite is a ZSM-5 zeolite.

10. The method of claim 1, wherein the zeolite-binder mixture is heated to a temperature of from 400° C. to about 700° C.

11. The method of claim 1 further comprising adding water to the zeolite-binder mixture and shaping the zeolite-binder mixture.

12. The method of claim 1 wherein the zeolite is treated with a phosphorus compound to form a phosphorus-treated zeolite having a phosphorus content of from 0.01 to about 0.15 gram of phosphorus per gram of zeolite.

13. The method of claim 12 wherein the zeolite contains 10-oxygen ring pores.

14. The method of claim 12 wherein the zeolite is a ZSM-5 zeolite.

15. The method of claim 12 wherein the binder material is present in an amount of from about to about 99% by weight of the bound zeolite catalyst.

16. The method of claim 12 wherein the binder material contains from about 1% to 99% by weight alumina or clay or their combinations.

17. The method of claim 12 further comprising adding water to the zeolite-binder mixture and shaping the zeolite-binder mixture.

18. The method of claim 12 wherein the phosphorus-treated zeolite has a phosphorus content of from 0.07 to about 0.12 gram of phosphorus per gram of zeolite.

19. The method of claim 12 wherein the zeolite-binder mixture is heated to a temperature of from 400° C. to about 700° C.

20. A zeolite catalyst prepared by:
   a) treating a zeolite with a phosphorus compound to form a phosphorus-treated zeolite;
   b) treating an inorganic oxide binder material with a mineral acid;
   c) combining the phosphorus-treated zeolite with an inorganic oxide binder material to form a zeolite-binder mixture; and
   d) heating the zeolite-binder mixture at a temperature of from about 400° C. or higher to form a bound zeolite catalyst.

21. The zeolite catalyst of claim 20 wherein the phosphorus-treated zeolite has a phosphorus content of from 0.01 to about 0.15 gram of phosphorus per gram of zeolite.

22. The zeolite catalyst of claim 20 wherein the binder material includes at least one of alumina, clay, aluminum phosphate and silica-alumina.

23. The zeolite catalyst of claim 20 wherein the binder material is an alumina-containing material.

24. The zeolite catalyst of claim 20 wherein the binder material is present in an amount of from about 1% to about 99% by weight of the bound zeolite catalyst.

25. The zeolite catalyst of claim 20 wherein the binder material contains from about 1% to 99% by weight alumina.

26. The zeolite catalyst of claim 20 wherein the zeolite contains 10-oxygen ring pores.

27. The zeolite catalyst of claim 20 wherein the zeolite is a ZSM-5 zeolite.

28. The zeolite catalyst of claim 20 wherein the zeolite-binder mixture is heated to a temperature of from 400° C. to about 700° C.

29. The zeolite catalyst of claim 20 further comprising adding water to the zeolite-binder mixture and shaping the zeolite-binder mixture.

30. A zeolite catalyst comprising:
   a phosphorus-containing zeolite that is bound with an inorganic oxide binder which has been treated with a mineral acid prior to being bound with the phosphorus-containing zeolite, and wherein the bound zeolite has been calcined at 400° C. or higher.

31. The zeolite catalyst of claim 30 wherein the mineral acid is hydrochloric acid, nitric acid, phosphoric acid or sulfuric acid.

32. The zeolite catalyst of claim 31 wherein the mineral acid is nitric acid.

33. The zeolite catalyst of claim 30 wherein the binder material is at least one of alumina, clay, aluminum phosphate or silica-alumina.

34. The zeolite catalyst of claim 30 wherein the binder material is alumina.

35. The zeolite catalyst of claim 30 wherein the binder material is present in an amount of from about 1% to about 99% by weight of the bound zeolite catalyst.

36. The zeolite catalyst of claim 30 wherein the binder material contains from about 1% to 99% by weight alumina.

37. The zeolite catalyst of claim 30 wherein the zeolite contains 10-oxygen ring pores.

38. The zeolite catalyst of claim 30 wherein the zeolite is a ZSM-5 zeolite.

39. The zeolite catalyst of claim 30 wherein the phosphorus-treated zeolite has a phosphorus content of from 0.01 to about 0.15 gram of phosphorus per gram of zeolite.

40. A method of preparing an alkyl aromatic product comprising:
 a) treating a zeolite with a phosphorus compound to form a phosphorus-treated zeolite;
 b) treating an inorganic oxide binder material with a mineral acid;
 c) combining the phosphorus-treated zeolite with an inorganic oxide binder material to form a zeolite-binder mixture;
 d) heating the zeolite-binder mixture at temperature of about 400° C. or higher to form a bound zeolite catalyst; and
 e) contacting the bound zeolite catalyst with an aromatic alkylation feed of an aromatic compound and an alkylating agent under reaction conditions suitable for aromatic alkylation.

41. The method of claim 40 wherein the binder material includes at least one of alumina, clay, aluminum phosphate and silica-alumina.

42. The method of claim 40 wherein the binder material is an alumina-containing material.

43. The method of claim 40 wherein the binder material is present in an amount of from about 1% to about 99% by weight of the bound zeolite catalyst.

44. The method of claim 40 wherein the binder material contains from about 1% to 99% by weight alumina or clay or their combinations.

45. The method of claim 40 wherein the zeolite is a ZSM-5 zeolite.

46. The method of claim 40 wherein the zeolite-binder mixture is heated to a temperature of from 400° C. to about 700° C.

47. The method of claim 40 further comprising adding water to the zeolite-binder mixture and shaping the zeolite-binder mixture.

48. The method of claim 40 wherein the aromatic compound is toluene.

49. The method of claim 40 wherein the aromatic compound is toluene and the alkylating agent is methanol.

50. The method of claim 40 wherein the zeolite is treated with a phosphorus compound to form a phosphorus-treated zeolite having a phosphorus content of from 0.01 to about 0.15 gram of phosphorus per gram of zeolite.

51. The method of claim 50 wherein the zeolite is a ZSM-5 zeolite.

52. The method of claim 51 wherein the binder material includes at least one of alumina, clay, aluminum phosphate and silica-alumina.

53. The method of claim 51 wherein the binder material is an alumina-containing material.

54. The method of claim 51 wherein the binder material is present in an amount of from about 1% to about 99% by weight of the bound ZSM-5 zeolite catalyst.

55. The method of claim 51 wherein the binder material contains from about 1% to 99% by weight alumina.

56. The method of claim 50 wherein the zeolite-binder mixture is heated to a temperature of from 400° C. to about 700° C.

57. The method of claim 49 further comprising steaming the bound ZSM-5 zeolite at a temperature of 300° C. or less prior to contacting with the feed of toluene.

58. The method of claim 40 wherein the mineral acid is hydrochloric acid, nitric acid, phosphoric acid or sulfuric acid.

59. The method of claim 58 wherein the mineral acid is nitric acid.

60. The method of claim 1 additionally comprising:
 b) treating an inorganic oxide binder material with a sufficient amount of liquid mineral acid to form a mixture between the inorganic binder material and the liquid mineral acid in which there is no excess liquid.

61. The zeolite catalyst of claim 20 additionally comprising:
 b) treating an inorganic oxide binder material with a sufficient amount of liquid mineral acid to form a mixture between the inorganic binder material and the liquid mineral acid in which there is no excess liquid.

62. The zeolite catalyst of claim 30 additionally comprising:
 a phosphorus-containing zeolite that is bound with an inorganic oxide binder which has been treated with a sufficient amount of liquid mineral acid to form a mixture between the inorganic binder material and the liquid mineral acid in which there is no excess liquid prior to being bound with the phosphorus-containing zeolite.

* * * * *